US005563310A

United States Patent [19]

Chang et al.

[11] Patent Number: 5,563,310
[45] Date of Patent: * Oct. 8, 1996

[54] TOLUENE ALKYLATION WITH METHANOL

[75] Inventors: Clarence D. Chang, Princeton; Frank T. DiGuiseppi, Yardville; Scott Han, Lawrenceville, all of N.J.

[73] Assignee: Mobil Oil Corporation, Fairfax, Va.

[ * ] Notice: The portion of the term of this patent subsequent to Dec. 28, 2014, has been disclaimed.

[21] Appl. No.: 433,879

[22] Filed: May 2, 1995

Related U.S. Application Data

[63] Continuation-in-part of Ser. No. 365,335, Dec. 28, 1994, which is a continuation of Ser. No. 120,493, Sep. 14, 1993, abandoned.

[51] Int. Cl.$^6$ .............................. C07C 2/86; C07C 2/00
[52] U.S. Cl. ........................................ 585/467; 585/446
[58] Field of Search ................................ 585/446, 463, 585/467, 475

[56] References Cited

U.S. PATENT DOCUMENTS

| | | | |
|---|---|---|---|
| 4,259,537 | 3/1981 | Chu | 585/467 |
| 4,673,767 | 6/1987 | Nimry et al. | 585/467 |
| 5,157,199 | 10/1992 | Soled et al. | 585/750 |
| 5,248,841 | 9/1993 | Young | 585/467 |
| 5,345,026 | 9/1994 | Chang et al. | 585/700 |
| 5,382,731 | 1/1995 | Chang et al. | 585/315 |
| 5,396,011 | 3/1995 | Kuhn | 585/455 |
| 5,401,478 | 3/1995 | Chang et al. | 423/235 |

FOREIGN PATENT DOCUMENTS

| | | |
|---|---|---|
| 585065A1 | 8/1992 | European Pat. Off. . |
| 1-288339 | 11/1989 | Japan . |
| WO94/14732 | 7/1994 | WIPO . |

OTHER PUBLICATIONS

Hino M. et al. "Synthesis of Solid Superacid of Tungsten Oxides Supported on Zirconia and Its Catalytic Action for Reactions of Butane and Pentane," J. Chem. Soc., Chem. Commun.,, 1259–1260 (1988).

Proceedings 9th Intern. Congress on Catalysis, vol. 4, Oxide Catalyst and Catalyst Development, M. J. Phillips et al., ed., 1727–1734 (1988).

Iglesia, E., Soled, S. L., and Kramer, G. M. Isomerization of Alkanes on Sulfated Zirconia: Promotion by Pt and by Adamantyl Hydride Transfer Species, Journal of Catalysts 144, 238–253 (1993).

Hsu, C. Y., Heimbuch, C. R. Armes, C. T., and Gates, B. C., "A Highly Active Solid Superacid Catalyst for n–Butane Isomerization: A Sulfated Oxide Containing Iron, Manganese and Zirconium," J. Chem. Soc., Commun., 1645–1646 (1992).

Primary Examiner—Ponnathapura Achutamurthy
Attorney, Agent, or Firm—Ronald A. Bleeker; Dennis P. Santini; Lori F. Cuomo

[57] ABSTRACT

A process for the conversion of toluene to xylenes by alkylation with methanol over an acidic solid catalyst with a Group IVB metal oxide modified with an oxyanion of a Group VIB metal.

10 Claims, No Drawings

5,563,310

TOLUENE ALKYLATION WITH METHANOL

REFERENCE TO RELATED APPLICATIONS

This application is a continuation-in-part of application Ser. No. 08/365,335, filed Dec. 28, 1994, which is a continuation of application Ser. No. 08/120,493 filed Sep. 14, 1993, now abandoned, incorporated herein by reference. This application is related by subject matter to application Ser. No. 08/344,327, filed Nov. 23, 1994, now U.S. Pat. No. 5,516,954, and application Ser. No. 08/228,772, filed Apr. 18, 1994, now U.S. Pat. No. 5,449,947.

FIELD OF THE INVENTION

The process of the present invention relates to the alkylation of toluene with methanol to form xylenes, in particular ortho-xylene, over a catalyst comprising an acidic solid comprising a Group IVB metal oxide modified with an oxyanion of a Group VIB metal.

DETAILED DESCRIPTION OF THE INVENTION

The acidic solid material useful as a catalyst in the present process may be prepared in accordance with U.S. patent application Ser. Nos. 08/332,169, filed Oct. 31, 1994; 08/236,073, filed May 2, 1994; 08/143,716, filed Nov. 1, 1993; and 08/136,838, filed Oct. 18, 1993, the entire disclosures incorporated herein by reference.

The solid material described herein comprises an oxide of a Group IVB metal, preferably zirconia or titania. This Group IVB metal oxide is modified with an oxyanion of a Group VIB metal, such as an oxyanion of tungsten, such as tungstate. The modification of the Group IVB metal oxide with the oxyanion of the Group VIB metal imparts acid functionality to the material. The modification of a Group IVB metal oxide, particularly, zirconia, with a Group VIB metal oxyanion, particularly tungstate, is described in U.S. Pat. No. 5,113,034; in Japanese Kokai Patent Application No. Hei 1 [1989]-288339; and in an article by K. Arata and M. Hino in *Proceeding 9th International Congress on Catalysis*, Volume 4, pages 1727–1735 (1988), the entire disclosures of these publications are expressly incorporated herein by reference. According to these publications, tungstate is impregnated onto a preformed solid zirconia material.

For the purposes of the present disclosure, the expression, Group IVB metal oxide modified with an oxyanion of a Group VIB metal, is intended to connote a material comprising, by elemental analysis, a Group IVB metal, a Group VIB metal and oxygen, with more acidity than a simple mixture of separately formed Group IVB metal oxide mixed with a separately formed Group VIB metal oxide or oxyanion. The present Group IVB metal, e.g., zirconium, oxide modified with an oxyanion of a Group VIB metal, e.g., tungsten, is believed to result from an actual chemical interaction between a source of a Group IVB metal oxide and a source of a Group VIB metal oxide or oxyanion.

This chemical interaction is discussed in the aforementioned article by K. Arata and M. Hino in *Proceedings 9th International Congress on Catalysis*, Volume 4, pages 1727–1735 (1988). In this article, it is suggested that solid superacids are formed when sulfates are reacted with hydroxides or oxides of certain metals, e.g., Zr. These superacids are said to have the structure of a bidentate sulfate ion coordinated to the metal, e.g., Zr. In this article, it is further suggested that a superacid can also be formed when tungstates are reacted with hydroxides or oxides of Zr. The resulting tungstate modified zirconia materials are theorized to have an analogous structure to the aforementioned superacids comprising sulfate and zirconium, wherein tungsten atoms replace sulfur atoms in the bidentate structure. It is further suggested that the tungsten oxide combines with zirconium oxide compounds to create superacid sites at the time the tetragonal phase is formed.

Although it is believed that the present catalysts may comprise the bidentate structure suggested in the aforementioned article by Arata and Hino, the particular structure of the catalytically active site in the present Group IVB metal oxide modified with an oxyanion of a Group VIB metal has not yet been confirmed, and it is not intended that this catalyst component should be limited to any particular structure.

Suitable sources of the Group IVB metal oxide, used for preparing the catalyst, include compounds capable of generating such oxides, such as oxychlorides, chlorides, nitrates, oxynitrates, etc., particularly of zirconium or titanium. Alkoxides of such metals may also be used as precursors or sources of the Group IVB metal oxide. Examples of such alkoxides include zirconium n-propoxide and titanium i-propoxide. These sources of a Group IVB metal oxide, particularly zirconia, may form zirconium hydroxide, i.e., $Zr(OH)_4$, or hydrated zirconia as intermediate species upon precipitation from an aqueous medium in the absence of a reactive source of tungstate. The expression, hydrated zirconia, is intended to connote materials comprising zirconium atoms covalently linked to other zirconium atoms via bridging oxygen atoms, i.e., Zr—O—Zr, further comprising available surface hydroxy groups. When hydrated zirconia is impregnated with a suitable source of tungstate under sufficient conditions, these available surface hydroxyl groups are believed to react with the source of tungstate to form an acidic catalyst. As suggested in the aforementioned article by K. Arata and M. Hino in *Proceedings 9th International Congress on Catalysis*, Volume 4, pages 1727–1735 (1988), precalcination of $Zr(OH)_4$ at a temperature of from about 100° C. to about 400° C. results in a species which interacts more favorably with tungstate upon impregnation therewith. This precalcination is believed to result in the condensation of ZrOH groups to form a polymeric zirconia species with surface hydroxyl groups. This polymeric species is referred to herein as a form of a hydrated zirconia.

Suitable sources for the oxyanion of the Group VIB metal, preferably molybdenum or tungsten, include, but are not limited to, ammonium metatungstate or metamolybdate, tungsten or molybdenum chloride, tungsten or molybdenum carbonyl, tungstic or molybdic acid and sodium tungstate or molybdate.

The present catalyst may be prepared, for example, by impregnating the hydroxide or oxide, particularly the hydrated oxide, of the Group IVB metal with an aqueous solution containing an anion of the Group VIB metal, preferably tungstate or molybdate, followed by drying.

The present modified oxide material may also be prepared by treatment of a hydrated Group IVB metal oxide, such as hydrated zirconia, under sufficient hydrothermal conditions prior to contact with a source of a Group VIB metal oxyanion, such as tungstate. More particularly, refluxing hydrated zirconia in an aqueous solution having a pH of 7 or greater was beneficial. Without wishing to be bound by any theory, it is theorized that the hydrothermally treated, hydrated zirconia is better because it has higher surface area. It is also theoretically possible that the hydrothermal treatment alters surface hydroxyl groups on the hydrated zirconia, possibly in a manner which promotes a more desirable interaction with the source of tungstate later used.

The hydrothermal conditions may include a temperature of at least 50° C., e.g., at least 80° C., e.g., at least 100° C. The hydrothermal treatment may take place in a sealed vessel at greater than atmospheric pressure. However, a preferred mode of treatment involves the use of an open vessel under reflux conditions. Agitation of hydrated Group IVB metal oxide in the liquid medium, e.g., by the action of refluxing liquid and/or stirring, promotes the effective interaction of the hydrated oxide with the liquid medium. The duration of the contact of the hydrated oxide with the liquid medium may be at least 1 hour, e.g., at least 8 hours. The liquid medium for this treatment may have a pH of 7 or greater, e.g., 9 or greater. Suitable liquid mediums include water, hydroxide solutions (including hydroxides of $NH_4^+$, $Na^+$, $K^+$, $Mg^{2+}$, and $Ca^{2+}$), carbonate and bicarbonate solutions (including carbonates and bicarbonates of $NH_4^+$, $Na^+$, $K^+$, $Mg^{2+}$, and $Ca^{2+}$) pyridine and its derivatives, and alkyl/hydroxyl amines.

The present modified oxide material may also be prepared by combining a first liquid solution comprising a source of a Group IVB metal oxide with a second liquid solution comprising a source of an oxyanion of a Group VIB metal. This combination of two solutions takes place under conditions sufficient to cause co-precipitation of the modified oxide material as a solid from the liquid medium. Alternatively, the source of the Group IVB metal oxide and the source of the oxyanion of the Group VIB metal may be combined in a single liquid solution. This solution may then be subjected to conditions sufficient to cause co-precipitation of the solid modified oxide material, such as by the addition of a precipitating reagent to the solution. Water is a preferred solvent for these solutions.

The temperature at which the liquid medium is maintained during the co-precipitation may be less than about 200° C., e.g., from about 0° C. to about 200° C. This liquid medium may be maintained at an ambient temperature (i.e., room temperature) or the liquid may be cooled or heated. A particular range of such temperatures is from about 50° C. to about 100° C.

The liquid medium from which the present catalyst components are co-precipitated may optionally comprise a solid support material, in which case the present catalyst may be co-precipitated directly onto the solid support material. Examples of such support materials include the material designated M41S, which is described in U.S. Pat. No. 5,102,643. A particular example of such an M41S material is a material designated MCM-41, which is described in U.S. Pat. No. 5,098,684.

Support materials and/or co-catalyst materials may also, optionally, be co-precipitated from the liquid medium along with the Group IVB metal oxide and the oxyanion of the Group VIB metal. An example of a co-catalyst material is a hydrogenation/dehydrogenation component.

According to an optional modification of the solid material described herein, a hydrogenation/dehydrogenation component is combined with the material. This hydrogenation/dehydrogenation component imparts the ability of the material to catalyze the addition of hydrogen to or the removal of hydrogen from organic compounds, such as hydrocarbons, optionally substituted with one or more heteroatoms, such as oxygen, nitrogen, metals or sulfur, when the organic compounds are contacted with the modified material under sufficient hydrogenation or dehydrogenation conditions.

Examples of hydrogenation/dehydrogenation components include the oxide, hydroxide or free metal (i.e., zero valent) forms of Group VIII metals (i.e., Pt, Pd, Ir, Rh, Os, Ru, Ni, Co and Fe), Group IVA metals (i.e., Sn and Pb), Group VB metals (i.e., Sb and Bi) and Group VIIB metals (i.e., Mn, Tc and Re). The present catalyst may comprise one or more catalytic forms of one or more noble metals (i.e., Pt, Pd, Ir, Rh, Os or Ru). Combinations of catalytic forms of such noble or non-noble metals, such as combinations of Pt with Sn, may be used. The valence state of the metal of the hydrogenation/dehydrogenation component is preferably in a reduced valance state, e.g., when this component is in the form of an oxide or hydroxide. The reduced valence state of this metal may be attained, in situ, during the course of a reaction, when a reducing agent, such as hydrogen, is included in the feed to the reaction.

Other elements, such as alkali (Group IA) or alkaline earth (Group IIA) compounds may optionally be added to or co-precipitated with the present catalyst to alter catalytic properties. The addition of such alkali or alkaline earth compounds to the present catalyst may enhance the catalytic properties of components thereof, e.g., Pt or W, in terms of their ability to function as a hydrogenation/dehydrogenation component or an acid component.

The Group IVB metal (i.e., Ti, Zr or Hf) and the Group VIB metal (i.e., Cr, Mo or W) species of the present catalyst are not limited to any particular valence state for these species. These species may be present in this catalyst in any possible positive oxidation value for these species. Subjecting the catalyst, e.g., when the catalyst comprises tungsten, to reducing conditions, e.g., believed to be sufficient to reduce the valence state of the tungsten, may enhance the overall catalytic ability of the catalyst to catalyze certain reactions, e.g., the isomerization of n-hexane.

The modified acidic oxide may be contacted with hydrogen at elevated temperatures. These elevated temperatures may be 100° C. or greater, e.g., 250° C. or greater, e.g., about 300° C. The duration of this contact may be as short as one hour or even 0.1 hour. However, extended contact may also be used. This extended contact may take place for a period of 6 hours or greater, e.g., about 18 hours. When zirconia is modified with tungstate and then contacted with hydrogen at elevated temperatures, an increase in catalytic activity, e.g., for paraffin isomerization, has been observed. The modified acidic oxide may be contacted with hydrogen in the presence or absence of a hydrocarbon cofeed. For example, the activity of the catalyst may be increased, in situ, during the course of a reaction, such as hydrocracking, when a hydrocarbon and hydrogen are passed over the catalyst at elevated temperatures.

The optional hydrogenation/dehydrogenation component of the present catalyst may be derived from Group VIII metals, such as platinum, iridium, osmium, palladium, rhodium, ruthenium, nickel, cobalt, iron and mixtures of two or more thereof. Optional components of the present catalyst, which may be used alone or mixed with the above-mentioned hydrogenation/dehydrogenation components, may be derived from Group IVA metals, preferably Sn, and/or components derived from Group VIIB metals, preferably rhenium and manganese. These components may be added to the catalyst by methods known in the art, such as ion exchange, impregnation or physical admixture. For example, salt solutions of these metals may be contacted with the remaining catalyst components under conditions sufficient to combine the respective components. The metal containing salt is preferably water soluble. Examples of such salts include chloroplatinic acid, tetraammineplatinum complexes, platinum chloride, tin sulfate and tin chloride. The optional components may also be co-precipitated along with the other components of the modified oxide material.

When the present tungstate-modified zirconia catalyst is impregnated with platinum to form a catalyst particularly adapted to catalyze paraffin isomerization reactions, it has been discovered that it is desirable to co-precipitate about one percent by weight of Fe or Mn along with the solid precipitated from the aqueous mixture comprising the source of zirconia and the source of tungstate. Suitable iron salts, which may be included in this aqueous mixture, include $Fe(NO_3)_3$ and $Fe_2(SO_4)_3$.

The present modified oxide material may be recovered by filtration from the liquid medium, followed by drying. Calcination of the resulting material may be carried out, preferably in an oxidizing atmosphere, at temperatures from about 500° C. to about 900° C., preferably from about 700° C. to about 850° C., and more preferably from about 750° C. to about 825° C. The calcination time may be up to 48 hours, preferably for about 0.1–24 hours, and more preferably for about 1.0–10 hours. In a most preferred embodiment, calcination is carried out at about 800° C. for about 1 to about 3 hours. The optional components of the catalyst (e.g., Group VIII metal, Group VIIB metal, etc.) may be added after or before the calcination step by techniques known in the art, such as impregnation, co-impregnation, co-precipitation, physical admixture, etc. The optional components, e.g., the hydrogenation/dehydrogenation component, may also be combined with the remaining catalyst components before or after these remaining components are combined with a binder or matrix material as described hereinafter.

In the present catalyst, of the Group IVB oxides, zirconium oxide is preferred; of the Group VIB anions, tungstate is preferred; and of the optional hydrogenation/dehydrogenation components, platinum and/or platinum-tin are preferred.

Qualitatively speaking, elemental analysis of the present acidic solid will reveal the presence of Group IVB metal, Group VIB metal and oxygen. The amount of oxygen measured in such an analysis will depend on a number of factors, such as the valence state of the Group IVB and Group VIB metals, the form of the optional hydrogenation/dehydrogenation component, moisture content, etc. Accordingly, in characterizing the composition of the present catalyst, it is best not to be restricted by any particular quantities of oxygen. In functional terms, the amount of Group VIB oxyanion in the present catalyst may be expressed as that amount which increases the acidity of the Group IVB oxide. This amount is referred to herein as an acidity increasing amount. Elemental analysis of the present catalyst may be used to determine the relative amounts of Group IVB metal and Group VIB metal in the catalyst. From these amounts, mole ratios in the form of $XO_2/YO_3$ may be calculated, where X is said Group IVB metal, assumed to be in the form $XO_2$, and Y is said Group VIB metal, assumed to be in the form of $YO_3$. It will be appreciated, however, that these forms of oxides, i.e., $XO_2$ and $YO_3$, may not actually exist, and are referred to herein simply for the purposes of calculating relative quantities of X and Y in the present catalyst. The present catalysts may have calculated mole ratios, expressed in the form of $XO_2/YO_3$, where X is at least one Group IVB metal (i.e., Ti, Zr, and Hf) and Y is at least one Group VIB metal (i.e., Cr, Mo, or W), of up to 1000, e.g., up to 300, e.g., from 2 to 100, e.g., from 4 to 30.

The amount of iron and/or manganese which is incorporated into the present acidic solid may also be expressed in terms of calculated mole ratios of oxides, based upon the elemental analysis of the solid for the Group IVB metal, X, along with Mn and Fe. More particularly, this acidic solid may have a calculated mole ratio, expressed in terms of $XO_2/(MnO_2+Fe_2O_3)$, of, for example, from 10 to 500. It will be appreciated, however, that Mn need not necessarily be in the form of $MnO_2$, and Fe need not be in the form of $Fe_2O_3$. More particularly, at least a portion of these components may be in the form of free metals or other combined forms than $MnO_2$ or $Fe_2O_3$ e.g., as salts with elements other than oxygen, in any possible valence state for X, Mn, or Fe. Accordingly, it will be understood that the expression, $XO_2/(MnO_2+Fe_2O_3)$, is given merely for the purposes of expressing calculated quantities of X, Mn, and Fe, and is not to be construed as being limited of the actual form of these elements in the present acidic solid material.

The amount of optional hydrogenation/dehydrogenation component may be that amount which imparts or increases the catalytic ability of the overall material to catalytically hydrogenate or dehydrogenate a hydrogenatable or dehydrogenatable organic compound under sufficient hydrogenation or dehydrogenation conditions. This amount is referred to herein as a catalytic amount. Quantitatively speaking, the present catalyst may comprise, for example, from about 0.001 to about 5 wt %, e.g., from about 0.1 to about 2 wt %, of the optional hydrogenation/dehydrogenation component, especially when this component is a noble metal.

Especially when the present catalyst includes a platinum hydrogenation/dehydrogenation component, this catalyst may also comprise up to about five weight percent of Fe and/or Mn, as measured by elemental analysis of the catalyst.

The present catalyst is acidic and may be observed as being highly acidic, even to the extent of being a superacid. Superacids are a known class of acidic materials which have an acidity greater than that of 100% $H_2SO_4$. This level of acidity may be determined by any appropriate means, including the use of suitable indicators, the determination of the ability to protonate certain chemicals, and/or the determination of the ability to stabilize certain cations, especially certain carbonium or carbenium ions. For example, this catalyst, whether analyzed in the presence or absence of optional components (e.g., hydrogenation/dehydrogenation components) and/or binder materials, may have an acid strength of a superacid as measured by the color change of an appropriate indicator, such as the Hammett indicator. More particularly, the Ho acid strength of the present catalyst may have a value of less than −13, i.e., an "acid strength" of greater than −13. The use of Hammett indicators to measure the acidity of solid superacids is discussed in the Soled et al. U.S. Pat. No. 5,157,199. This Soled et al. patent also describes the Ho acid strength for certain sulfated transition metal superacids.

The catalyst described herein may be used in the alkylation of toluene with methanol to form xylenes and in particular ortho-xylene.

The desired xylene products are formed in high yields, greater than about 5 wt. % xylenes, over the catalyst of the present invention. Further, the catalyst of the present invention is selective towards ortho-xylene with a selectivity of about 40% or higher. Alkylation of toluene in the presence of the above described catalysts can be effected by contact of toluene with methanol as an alkylating agent. Alcohols (inclusive of monoalcohols, dialcohols, trialcohols, etc.) such as ethanol, the propanols, the butanols and the pentanols may also be used.

The reaction is carried out at a temperature in the range of from about 100 to about 800° C. and at a pressure in the range of from about 100 to about 1500 psig. The weight hourly space velocity (WHSV) is in the range of from about 0.1 to about 1000, preferably in the range of from about 1 to about 20. The molar ratio of toluene to methanol is generally in the range of from about 0.1:1 to about 50:1.

The following examples illustrate the process of the present invention.

EXAMPLE 1

This Example describes the preparation of a $WO_x/ZrO_2$ catalyst. One part by weight of zirconyl chloride, $ZrOCl_2.8SH_2O$, was dissolved in 10 parts $H_2O$ and concentrated $NH_4OH_{(aq)}$ added until the solution pH was ~9. The resulting slurry, $Zr(OH)_4$, was filtered and washed with 10 parts of distilled, deionized water. The solid was air dried at 130° C. for 16 hours. One part by weight of the filtered wet cake was mixed with 10 parts of distilled, deionized water and the pH of the mixture set to pH ~9 with concentrated $NH_4OH_{(aq)}$. This mixture was refluxed for 16 hours, cooled, filtered, and washed with 10 parts of water. The solid was air dried at 130° C. for 16 hours. Approximately 3.4 parts by weight of the dried product was impregnated via incipient wetness with 2.6 parts of an aqueous solution containing 1 part of ammonium metatungstate. The resulting material was dried in air and then calcined at 825° C. in air for 3 hours.

EXAMPLE 2

The catalyst at 300° C. for 18 hours prepared in accordance with Example 1 was activated with $H_2$. The reactor was brought to the desired conditions with $H_2$ and a toluene/methanol feedstream was passed over the catalyst. All runs were conducted under 600 psig, 4 WHSV and 2 mol/mol $H_2$/toluene. Temperature, toluene:methanol feed ratios and catalytic results are given below in Table 1.

TABLE 1

| RUN | 1 | 2 | 3 | 4 | 5 |
|---|---|---|---|---|---|
| Feed Ratio (mol/mol) | 8:1 | 8:1 | 8:1 | 4:1 | 4:1 |
| Temperature, °C. | 200 | 215 | 230 | 230 | 235 |
| Toluene conversion, wt. % | 5.3 | 8.4 | 11.6 | 11.8 | 11.4 |
| Methanol conversion, wt. % | 92.5 | 97.3 | 95.7 | 97.0 | 93.6 |
| Xylene yield, wt. % | 5.8 | 8.1 | 9.4 | 9.6 | 10.7 |
| p-Xylene selectivity, % | 29.0 | 29.1 | 29.1 | 28.2 | 28.8 |
| m-Xylene selectivity, % | 20.8 | 21.0 | 21.5 | 21.4 | 21.0 |
| o-Xylene selectivity, % | 50.2 | 49.9 | 49.4 | 50.4 | 50.2 |

The data in Table 1 show about 5 to about 11% xylenes yield depending on reaction severity. The predominant xylene isomer formed is ortho-xylene, with low selectivities (about 20% –30%) each to the para-xylene and meta-xylene isomer. Methanol conversions in all runs exceeded 90%.

EXAMPLE 3

A W-ZSM-5 catalyst was prepared according to the method described in Example 5 of U.S. Pat. No. 4,259,537. The catalyst was activated with $H_2$ at 300° C. for 18 hours.

The reactor was brought to the desired conditions with $H_2$ and a toluene/methanol feedstream was passed over the catalyst. All runs were conducted under 600 psig, 4 WHSV and 2 mol/mol $H_2$/toluene. Temperature, toluene:methanol feed ratios and catalytic results are given below in Table 2.

TABLE 2

| RUN | 6 | 7 | 8 |
|---|---|---|---|
| Toluene:methanol feed ratio (mol/mol) | 4:1 | 8:1 | 8:1 |
| Temperature, °C. | 230 | 200 | 230 |
| Toluene conversion, wt. % | 1.0 | 0.0 | 2.0 |
| Methanol conversion, wt. % | 100.0 | 100.0 | 92.9 |
| Xylene yield, wt.% | 3.0 | 0.7 | 2.0 |
| p-Xylene selectivity, % | 22.9 | 21.2 | 29.8 |
| m-Xylene selectivity, % | 20.3 | 19.7 | 20.2 |
| o-Xylene selectivity, % | 56.8 | 59.1 | 50.0 |

The data show that the $WOx/ZrO_2$ catalyst of the present invention gives significantly higher toluene conversion and xylene yield than W-ZSM-5 under the same conditions.

The catalysts of the present invention have excellent activity for the alkylation of toluene with methanol. High selectivity to ortho-xylene with high total xylene yield greater than about 5 wt. % was also observed using the process of the present invention.

Changes and modifications in the specifically described embodiments can be carried out without departing from the scope of the invention which is intended to be limited only by the scope of the appended claims.

We claim:

1. A process for the conversion of toluene selective towards ortho-xylene which comprises contacting toluene with methanol under sufficient alkylation conditions in the presence of a alkylation catalyst, said catalyst comprising an acidic solid comprising a Group IVB metal oxide modified with an oxyanion of a Group VIB metal.

2. The process of claim 1, wherein said alkylation conditions include a temperature in the range of from about 100° to about 800 ° C., a pressure in the range of from about 100 to about 1500 psig and a WHSV in the range of from about 0.1 to about 20.

3. The process of claim 1, wherein the molar ratio of toluene to methanol is in the range of from about 0.1:1 to about 50:1.

4. The process of claim 1, wherein said Group IVB metal is Zr and wherein said Group VIB metal is W.

5. The process of claim 1, wherein said alkylation catalyst is pretreated prior to said conversion by treating with hydrogen.

6. The process of claim 1, wherein selectivity towards ortho-xylene is about 40% or higher.

7. The process of claim 1, wherein said alkylation catalyst is pretreated with $H_2$ prior to said contacting.

8. The process of claim 7, wherein the hydrogen pretreatment is at a temperature in the range of from about 100° C. to about 300° C.

9. The process of claim 1, wherein said alkylation catalyst comprises a hydrogenation/dehydrogenation component.

10. The process of claim 9, therein said hydrogen/dehydrogen component is selected from the group consisting of iron, manganese and platinum.

* * * * *